United States Patent [19]
Stoltze et al.

[11] Patent Number: 6,059,738
[45] Date of Patent: May 9, 2000

[54] GUIDEWIRE HAVING A COATED TIP

[75] Inventors: Jacob Stoltze, Copenhagen; Jorgen Kamstrup-Larsen, Allerod, both of Denmark

[73] Assignee: Meadox Medicals, Inc., Oakland, N.J.

[21] Appl. No.: 08/496,956

[22] Filed: Jun. 30, 1995

[51] Int. Cl.⁷ ...................................................... A61B 5/00
[52] U.S. Cl. ............................. 600/585; 604/95; 604/280
[58] Field of Search ............................... 600/585; 604/95, 604/96, 280, 281, 282

[56] References Cited

U.S. PATENT DOCUMENTS

| | | | |
|---|---|---|---|
| 4,642,267 | 2/1987 | Creasy et al. | 428/413 |
| 4,841,976 | 6/1989 | Packard et al. | 128/657 |
| 4,876,126 | 10/1989 | Takemura et al. | 428/35.7 |
| 4,884,579 | 12/1989 | Engelson | 128/772 |
| 4,925,445 | 5/1990 | Sakamoto et al. | 604/95 |
| 5,040,543 | 8/1991 | Baders et al. | 128/772 |
| 5,129,890 | 7/1992 | Bates et al. | 604/281 |
| 5,213,111 | 5/1993 | Cook et al. | 128/772 |
| 5,217,026 | 6/1993 | Stoy et al. | 128/772 |
| 5,275,173 | 1/1994 | Samson et al. | 128/772 |
| 5,304,140 | 4/1994 | Kugo et al. | 604/281 |
| 5,452,726 | 9/1995 | Burmeister et al. | 600/585 |

FOREIGN PATENT DOCUMENTS

| | | |
|---|---|---|
| 93094 A1 | 11/1983 | European Pat. Off. . |
| 389632 A1 | 10/1990 | European Pat. Off. . |
| 395098 A1 | 10/1990 | European Pat. Off. . |
| 407965 A1 | 1/1991 | European Pat. Off. . |
| 1435797 | 5/1976 | United Kingdom . |
| WO 91/19756 | 12/1991 | WIPO . |
| WO 93/08862 | 5/1993 | WIPO . |

*Primary Examiner*—Cary O'Connor
*Assistant Examiner*—Pamela L. Wingood
*Attorney, Agent, or Firm*—Hoffmann & Baron, LLP

[57] ABSTRACT

A guidewire includes a shaft portion and a tip portion with the tip portion having a plastic tubular coating thereover. The shaft portion of the guidewire has a given diameter and the tip portion has a diameter which decreases towards a distal end thereof. A tubular plastic coating is placed on at least the tip portion of the guidewire. The outer diameter of the coating on the tip portion exceeds the diameter of the shaft portion. The diameter of the plastic coating is reduced so as to be no greater than the diameter of the shaft portion. A hydrophilic coating may be applied over the shaft and the tip portion of the guidewire.

12 Claims, 3 Drawing Sheets

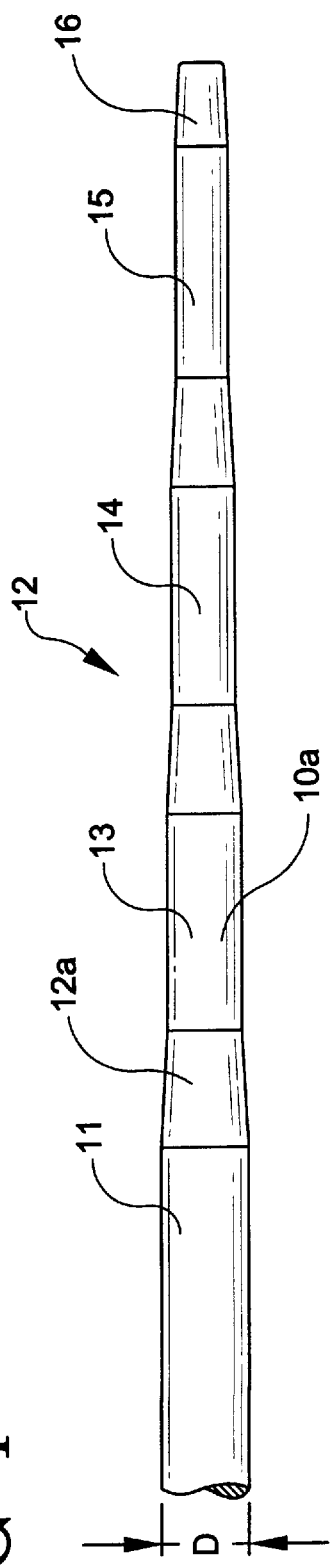
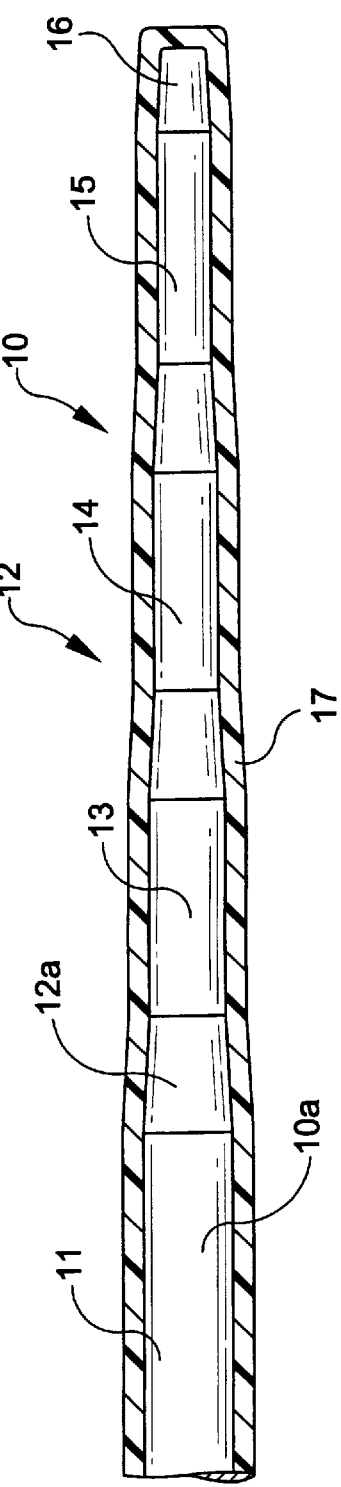

GUIDEWIRE HAVING A COATED TIP

FIELD OF THE INVENTION

The present invention relates generally to a guidewire for guiding a catheter through a body lumen such as the vascular system. More particularly, the present invention relates to a catheter guidewire having a coated distal tip portion which facilitates movement of the guidewire through the lumen.

BACKGROUND OF THE INVENTION

It has long been known to use guidewires for guiding catheters through body lumens for various medical procedures. One application in which such guidewires are typically used is in the percutaneous delivery of a catheter into the vascular system. The guidewire is a long flexible metal wire which may be inserted into the body percutaneously and advanced through the vascular system to the desired location. The guidewire may then be used as a vehicle for transporting an accompanying catheter to the given location.

In order to negotiate a tortuous path through the vascular system and to avoid obstacles during insertion, guidewires may include a curved flexible distal tip which can adapt itself to the shape of the blood vessel so that it can be advanced through such curved vessel without injuring the walls of the vessel. However, it is also important for the guidewire to exhibit sufficient rigidity such that the guidewire can be pushed forward without buckling or kinking. Further, proper advancement of the guidewire requires that the guidewire exhibit steerability. That is, the guidewire must be capable of being rotated so as to traverse curved portions of the vessel. Accordingly, the guidewire must also exhibit substantial torsional rigidity so that rotation of a proximate shaft portion causes corresponding rotation of the distal tip.

Guidewires of the type described herein are especially useful in procedures such as percutaneous transluminal coronary angioplasty (PTCA) and percutaneous transluminal angioplasty (PTA). In these procedures, the guidewires may be used to guide a balloon dilatation catheter to a stenosis in the blood vessel where upon the balloon of the guidewire is directed to the stenosis and the balloon is inflated thereby breaking apart the stenosed area of the vessel. Many guidewires, especially those used for PTCA procedures, are of relatively small diameter having an outer diameter not exceeding 0.018". The maximum diameter of a guidewire is limited by the internal diameter of the guidewire lumen in the balloon dilation catheter and by the vessel through which it must traverse.

The art has seen many attempts to provide guidewires which combine a relatively rigid shaft portion exhibiting substantial torsional rigidity and steerability and a flexible distal tip portion which facilitates traverse of the guidewire through the vascular system.

U.S. Pat. No. 4,925,445 describes a guidewire including a shaft portion and a distal tip portion which are formed from a superelastic TiNi alloy. The superelastic TiNi material enhances bendability and kink resistance of the guidewire. The entire guidewire may include a plastic coating thereover which enhances the ability of the guidewire to safely traverse the vascular system. The plastic coating may also contain an x-ray contrast medium such as metal particles therein which enhances the radiopacity of the guidewire.

However it has been found that with small sized guidewires such as those used for PCTA procedures, it is difficult to place a uniformly thin plastic coating thereover or if the guidewire is coated, the shaft may not exhibit the desired stiffness. Further, it is desirable in many instances to limit the plastic coating to the tip portion alone. This type of construction, with a coated tip portion and an uncoated shaft portion, helps transmit torque directly from the shaft portion to the tip portion resulting in enhanced steerability and maximum shaft stiffness. However, it is extremely difficult to coat only the flexible, thin distal tip portion of the guidewire. Attempts to coat the entire guidewire and selectively remove the coating from the shaft portion result in the coated tip portion having a larger diameter than the shaft portion.

It is also known to employ low friction hydrophilic coatings over guidewires. The hydrophilic coating increases the lubricity of the guidewire and allows the guidewire to more easily be maneuvered through tortuous areas of the vascular system. Examples of hydrophilic coatings in guidewire applications are found in U.S. Pat. Nos. 5,129,890 and 5,213,111.

However, none of the prior art techniques has been found to be suitable in providing a plastic coating at the distal tip of the guidewire where the overall diameter of the guidewire is not increased, so that the guidewire may still be used in locations requiring small diameters and allowing the guidewire to be passed through catheters having an internal luminal diameter which closely approximates the diameter of the shaft.

SUMMARY OF THE INVENTION

It is an object of the present invention to provide a method of forming a guidewire having a coated distal tip portion.

It is a further object of the present invention to provide a catheter guidewire having a proximal shaft portion and a distal tip portion and wherein the distal tip portion includes a coating thereover, the outer diameter of which is no greater than the diameter of the shaft portion.

It is a still further object of the present invention to provide a method of forming a catheter guidewire where a generally tubular coating is applied over the distal tip portion of the guidewire and the generally tubular coating is reduced so as to have a diameter no greater than the diameter of the shaft portion.

In the efficient attainment of these and other objects, the present invention provides a method of forming a guidewire assembly for a catheter. The method includes providing a guidewire having a proximal shaft portion and a distal tip portion where the diameter of the guidewire decreases from the shaft portion to the tip portion. A generally tubular coating is applied to at least the tip portion of the guidewire. The tubular coating has an outer diameter which is greater than the diameter of the shaft portion. The tubular coating is then reduced at the tip portion to a uniform outer diameter which is no greater than the diameter of the shaft portion.

As particularly described by way of the preferred embodiment herein, the reducing may be accomplished by centerless grinding where the tubular coating is ground to a uniform diameter no greater than the diameter of the shaft portion. Further, in the preferred embodiment, a hydrophilic coating may be disposed over the entire guidewire. The hydrophilic coating may be applied in two layers, a first layer of an acrylic latex applied directly over the guidewire and a second layer of a homo or copolymer of acrylic amide which is disposed over the first layer.

The present invention further provides a guidewire assembly including an elongate guidewire core. The core includes a proximal shaft portion of given diameter, a distal tip portion of diameter less than that of the shaft portion and a transition shoulder of decreasing diameter therebetween. A plastic coating extends over the distal tip portion and the transition shoulder. The plastic coating has an outer diameter that is no greater than substantially the outer diameter of the shaft portion.

As particularly disclosed, the plastic coating has a uniform diameter over the tip portion which is equal to the diameter of the uncoated shaft portion so that a smooth transition is provided over the transition shoulder.

As is further described herein, the tubular coating may include an x-ray contrast medium such as metal particles which increase the radiopacity of the coated guidewire. In addition, the metal particles also increase the decomposition temperature of the plastic coating without unduly increasing the viscosity of the melt for the formation of the plastic coating.

The guidewire of the present invention may be formed of stainless steel or a superelastic metallic material such as a TiNi alloy. Further, the shaft portion of the guidewire may be formed of stainless steel while the tip portion of the guidewire be formed from the superelastic metallic material.

BRIEF DESCRIPTION OF THE DRAWING

FIG. 1 shows in cross section an end extent of a wire used to form the guidewire assembly of the present invention.

FIG. 2 is a sectional showing similar to FIG. 1 of the guidewire assembly of the present invention including a plastic coating thereover.

DETAILED DESCRIPTION OF THE PREFERRED EMBODIMENTS

Figure 3:
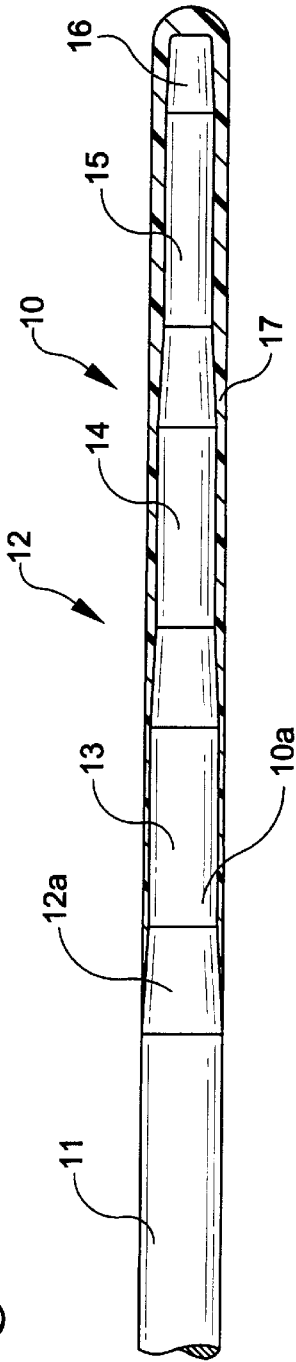
FIG. 3 is a sectional showing of a guidewire assembly of FIG. 2 with the plastic coating reduced in diameter.

The present invention as shown in the drawings includes a guidewire assembly 10 which comprises a guidewire core 10a and one or more coatings which will be described in detail hereinbelow.

Core 10a is an elongate generally cylindrical wire member having a proximal shaft portion 11 and a distal tip portion 12. The shaft portion 11 is generally uniformly cylindrical having a given outer diameter D. The tip portion 12 includes three longitudinally successive sections 13, 14 and 15 which extend respectively from shaft portion 11. Sections 13, 14 and 15 are of successively decreasing diameter. The furthest distal extent of core 10a ends in a distal tip end 16. Between tip portion 12 and shaft portion 11 a transition shoulder 12a is defined. Transition shoulder 12a is generally a tapered member tapering from a wider diameter adjacent shaft portion 11 to a narrower diameter adjacent tip portion 12.

Shaft portion 11 of core 10a, in the preferred embodiment, is formed of stainless steel. While other metals may also be used, stainless steel is preferred as it imparts sufficient rigidity to guidewire assembly 10 resulting in a high degree of torsional stability as well as pushability to enable the guidewire to be inserted through the vascular system.

The pushability of a guidewire is defined as the force necessary to push the guidewire a given distance through the vascular system. The pushability of a guidewire depends upon the resistance against deflection of the shaft when the distal end of the guidewire is abutted against an obstruction such as a stenosis or a curved portion of the vessel. The pushability of the guidewire allows the guidewire to be advanced past the obstruction or the curve without buckling or kinking.

The tip portion 12 of guidewire core 10a may also be formed from metal. In the preferred embodiment, tip portion 12 is formed from a superelastic (pseudoelastic) metallic material. As is well known, such superelastic material may include a titanium nickel (TiNi) alloy. The use of such a superelastic material allows for high flexural deformation to be obtained under a comparatively low load such that the tip portion 12 is capable of being highly flexed and returned to its original shape once the load has been relieved. The use of a superelastic tip portion 12 allows the guidewire to traverse a tortuous path through the vascular system without creating a permanent bend or kink in the tip portion. While TiNi is described as the preferred superelastic alloy, other well known superelastic alloys may also be employed. Further, it is contemplated that the entire guidewire core 10a may be formed of a uniform material of stainless steel or superelastic metal.

In order to render the guidewire assembly 10 more capable of easy traverse through the vascular system, the present invention provides for the placement of a coating on at least the tip portion 12 of guidewire assembly 10. As particularly shown in FIG. 2, a tubular plastic coating 17 is disposed over tip portion 12 and also may be placed over shaft portion 11. The tubular plastic coating 17 may be applied in a variety of known application techniques. One technique which may be employed to apply tubular coating 17 is to extrude the coating over core 10a which is passed through the center of an annular extrusion die to extrude the plastic thereover. Another technique may be to injection mold the tubular coating over core 10a or in the alternative, the core 10a may be repeatedly dipped in a suspension dispersion or solution of the material forming the coating. If the latter technique is used, each layer of coating is dried before an additional coating layer is applied. Additionally, the term "coating" as used hereinthroughout, shall also encompass the placement of a covering, such as a separate sheath over core 10a.

In a preferred embodiment, the tubular coating is a plastic coating which is preferably made from a polyether block amide but also may be formed from other materials such as an elastomer, polyethylene, polypropylene, polyvinylchloride, polyester, polyamide, polyurethane, fluorine plastics and silicone rubber or an elastomer or a composite material of the above-mentioned materials.

Further, the plastic coating 17 may include an x-ray contrast medium which enhances the radiopacity of the guidewire. Such x-ray contrast medium may include metal particles such as barium, tungsten, bismuth or lead particles which are present in the plastic coating 17 which is placed on core 10a.

The concentration of metal particles is preferably between 7 and 14% volume/volume and more preferably in a concentration of between 9 and 13.5% volume/volume. It is also preferable that the particle size of the metal particles be between 1 and 8 $\mu$m, especially where tungsten particles are used as the x-ray contrast medium.

The use of a relatively high concentration of metal particles in coating 17 in addition to improving the radiopacity of the guidewire assembly 10 also increases the decomposition temperature of the plastic material formed in the coating without unduly increasing the viscosity of melt or the formation of the plastic coating. Thus, the decomposition temperature of a preferred plastic coating containing tungsten particles of concentration of about 5.6% volume/volume is about 190° C. The decomposition temperature of the same plastic containing tungsten particles in concentrations of 7.3%, 10.9%, and 13.5% volume/volume is 196.4° C., 214.2° C. and 204.7° C. respectively. Thus, it can be seen that the decomposition temperature of the plastic is greatly increased by the addition of metal particles. It has been found that the viscosity of the plastic melt containing such increased amounts of tungsten is such that the momentum of such melt is between 1 and 10 nm determined by means of a Brabender mixer. Such viscosity has been found to be suitably acceptable for use in conventional extruders.

While the above technique is disclosed herein, x-ray contrast may also be achieved by placing one or more conventional gold rings or similar members directly on the tip core prior to placing the plastic coating thereon.

It is also preferred that the plastic coating 17 may contain additives such as an anticoagulating agent and an antithrombis material which facilitates use of the guidewire assembly in the vascular system.

In the efficient manufacture of the guidewire assembly 10 of the present invention, the plastic coating is placed on tip portion 12 and over shaft portion 11. Ultimately it is desirable to construct a guidewire assembly 10 with only the tip portion 12 including a plastic coating 17, as an uncoated shaft portion 11 allows torque to be transmitted to the tip portion directly with close to a 1:1 ratio and also obtains maximum shaft stiffness. However, in small sized guidewire (less than 0.018") having a thin flexible distal tip portion 12, it is extremely difficult to coat only the tip portion. The present invention therefore contemplates removal of that portion of the coating from the shaft portion 11 prior to further processing. The plastic coating may be removed from the shaft portion 11 by any well known technique. This results in an uncoated shaft portion 11. In addition to improving the torsional stability and shaft stiffness, removal of the plastic coating 17 from shaft portion 11 also results in the overall outer diameter of the core 10a being kept to a minimum.

Referring now to FIG. 3, the tubular coating 17 at tip portion 12 may now be reduced to a uniform outer diameter which does not exceed the outer diameter of shaft portion 11 of core 10a. In the preferred embodiment of the present invention, the tubular portion 17 is reduced to a desired uniform diameter which is substantially equal to the diameter D of the uncoated shaft portion 11. This results in a smooth transition between tip portion 12 and shaft portion 11 over transition shoulder 12a.

It has been found that a preferred process for the removal of the plastic coating 17 from tip portion 11 is by centerless grinding. Centerless grinding is a well known grinding technique which is typically used to impart cylindrical surfaces to elongate articles such as steel bars and the like that are either too long or too flexible for the ends of the bars to be mounted between center supports.

Figure 5:
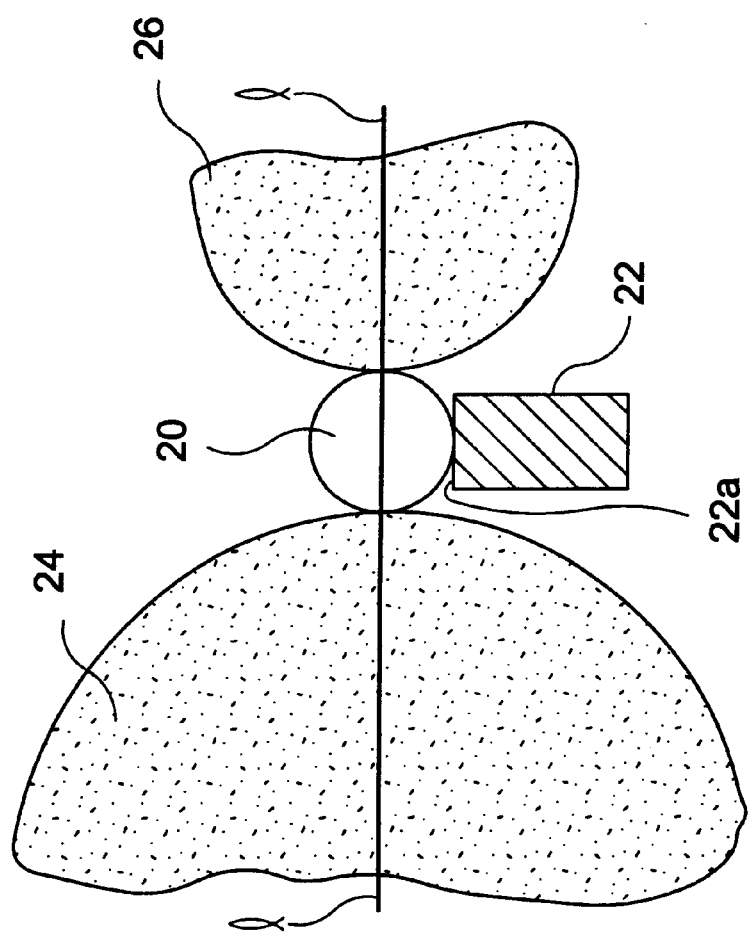
FIG. 5 is a schematic representation of a centerless grinding process used in accordance with the present invention.

As shown schematically in FIG. 5, in centerless grinding, the workpiece 20 rests on a work support blade 22 and is forced against the "grinding wheel" 24 by the "regulating" or "feed wheel" 26 which controls the speed of work rotation and the rate of work travel through the machine.

The centerline l of the wheels is the straight line joining the center of the grinding wheel 24 and the center of the regulating wheel 26 in the reference plane.

The reference plane is the plane perpendicular to the axis of the grinding wheel and passing through the point where the axis of the regulating wheel goes through the horizontal plane which runs through the axis of the grinding wheel.

In a plane perpendicular to the axis of the grinding wheel 24, the circle cutting the workpiece 20 is tangent to the two circles cutting the regulating wheel 26 and the grinding wheel 24 and to the perpendicular section through the bearing surface 22a of the blade 22.

While traditionally limited to steel bar stock and the like, it has been found that centerless grinding may be employed in accordance with the present invention for reducing the diameter of the plastic coating 17 applied to the tip portion 12 of a guidewire core 10a. It has further been found that with small sized guidewires such as that less than 0.018", the outer diameter of the plastic coating 17 can be uniformly reduced so as to obtain a tip portion 12 having both a radially and axially uniform coating thickness therealong.

Centerless grinding allows for the reduction of the tip portion 12, which would not otherwise be achievable due to the thin and flexible nature of the tip portion. The resulting guidewire has a uniform thickness and achieves a smooth transition between the tip portion 12 and shaft portion 11. In addition, the grinding process results in a uniform coating 17 being applied over tip portion 12 where the tip portion includes successive portions 13, 14 and 15 of longitudinally successive decreasing diameters. Thus, notwithstanding the tapering tip portion 12, the outer diameter of the plastic coating 17 remains constant therealong.

Centerless grinding has been found to be particularly suitable for the grinding of plastic coating 17 which contains an x-ray medium in the form of metallic particles.

As mentioned above, the present invention contemplates grinding the tubular coating 17 to an overall outer diameter which is substantially equal to diameter D (FIG. 1) of shaft portion 11 of core 10a. In this manner, while the distal tip portion 12 includes a coating 17 thereover, the coating does not increase the overall diameter of the core 10a thus allowing the guidewire assembly 10 to be used in areas where small sized guidewires are required.

Figure 4:
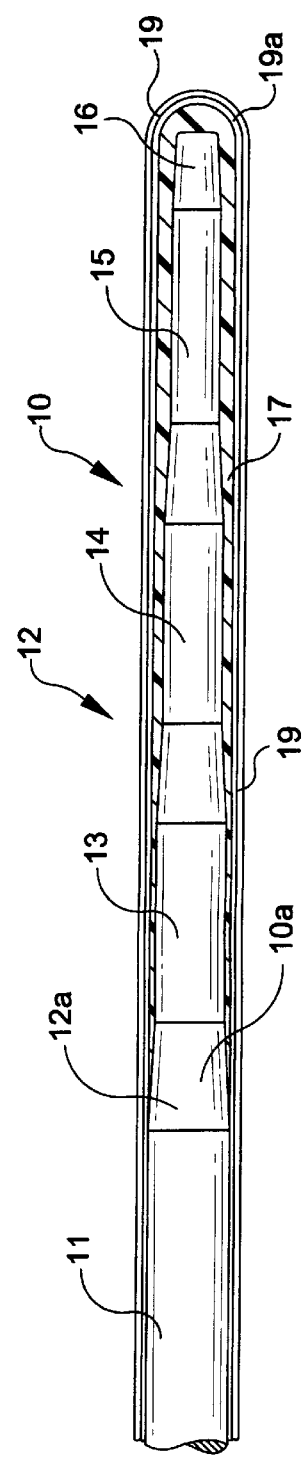
FIG. 4 is a sectional showing of the guidewire assembly of FIG. 3 including a hydrophilic coating placed thereover.

Optionally, to increase the lubricity of the guidewire assembly 10 so as to reduce friction between the guidewire assembly and the surrounding vascular structure through which it is inserted, a hydrophilic coating 19 such as shown in FIG. 4 may be employed. Hydrophilic coating 19 is of the type shown and described in commonly assigned International Patent Publication WO91/19756 which is incorporated by reference herein.

Hydrophilic coating 19 may be applied by applying a first inner layer of acrylic latex 19a and then applying a second outer layer of a homo or copolymer 19b of acrylic amide. However, other hydrophilic coating materials and techniques are also contemplated.

The invention may be further described with reference to the following example.

EXAMPLE

A metal wire consisting of a superelastic material of the type which is commercially available under the tradename Tynel BC, has a total length of about 63" and a diameter of about 0.014". The metal wire itself is subjected to centerless grinding so as to provide a distal tip having a length of about 16" comprising three successively tapering sections having diameters of about 0.013", 0.011" and 0.008". A tubular plastic coating having an outer diameter of about 0.020" on the shaft and an outer diameter of about 0.018" at the tip, is applied over the metal wire by extrusion. The plastic coating is prepared from a polyether block amide commercially available under the tradename PEBAX containing tungsten particles in a concentration of 10.9% volume/volume and having a decomposition temperature of 214.2° C. The metal wire is advanced through an orifice of an extruder at a speed of about 5 meters per minute. Subsequently the plastic coating is removed from the shaft of the metal wire and the plastic coated tip is mounted in a centerless grinding machine. The plastic coating is then ground and during the grinding process a coolant is supplied to the surface of the plastic coating to make it smooth. After grinding the outer diameter of the plastic coating is ground to 0.014" approximately the same diameter of the shaft portion of the metal wire. A thin uniform hydrophilic coating is then applied over the full length of the guidewire.

Various changes to the foregoing described and shown structures would now be evident to those skilled in the art. Accordingly, the particularly disclosed scope of the invention is set forth in the following claims.

What is claimed:

1. A guidewire assembly comprising:

an elongate guidewire core having a proximal shaft portion of a given outer diameter, a flexible distal tip portion of a diameter less than said given diameter and a transition shoulder of decreasing diameter therebetween, said shaft portion being capable of transmitting torque to said distal tip portion; and a plastic coating extending over said entire tip portion and said shoulder with said shaft portion being free of said plastic coating, said plastic coating having a uniform outer diameter which is no greater than substantially the given diameter of said shaft portion.

2. A guidewire assembly of claim 1 wherein said plastic coating has an outer diameter substantially equal to said given diameter of said shaft portion so as to create a smooth transition between said shaft portion and said tip portion over said transition shoulder.

3. A guidewire assembly of claim 2 wherein said distal tip portion includes longitudinally successive tip extents of decreasing diameter and wherein said plastic coating maintains a uniform outer diameter over said entire distal tip portion.

4. A guidewire assembly of claim 3 further including:

a hydrophilic coating disposed over said guidewire core, said hydrophilic coating covering said shaft portion and said plastic coating over said tip portion.

5. A guidewire assembly of claim 4 wherein said hydrophilic coating includes:

an inner layer of acrylic latex and an outer layer of a homo or copolymer.

6. A guidewire assembly of claim 1 wherein said shaft portion is formed from stainless steel.

7. A guidewire assembly of claim 6 wherein said tip portion is formed from stainless steel.

8. A guidewire assembly of claim 6 wherein said tip portion is formed of a superelastic metal.

9. A guidewire assembly of claim 8 wherein said superelastic metal is a TiNi alloy .

10. A guidewire assembly of claim 1 wherein said plastic coating includes an x-ray contrast medium.

11. A guidewire assembly of claim 10 wherein said x-ray contrast medium includes metal particles.

12. A guidewire assembly of claim 11 wherein said metal particles include tungsten particles having a particle size of between about 1 to 8 $\mu$m.

* * * * *